United States Patent
Otto

(10) Patent No.: US 7,094,399 B2
(45) Date of Patent: Aug. 22, 2006

(54) USE OF SPLICEOSOME MEDIATED RNA TRANS-SPLICING TO CONFER CELL SELECTIVE REPLICATION TO ADENOVIRUSES

(75) Inventor: Edward Otto, Great Falls, VA (US)

(73) Assignee: Intronn, Inc., Gaithersburg, MD (US)

( * ) Notice: Subject to any disclaimer, the term of this patent is extended or adjusted under 35 U.S.C. 154(b) by 0 days.

(21) Appl. No.: 10/434,727

(22) Filed: May 8, 2003

(65) Prior Publication Data

US 2004/0038403 A1    Feb. 26, 2004

Related U.S. Application Data

(60) Provisional application No. 60/378,690, filed on May 8, 2002.

(51) Int. Cl.
| | |
|---|---|
| A01N 63/00 | (2006.01) |
| A01N 65/00 | (2006.01) |
| C12N 15/00 | (2006.01) |
| C12N 15/09 | (2006.01) |
| C12N 15/63 | (2006.01) |
| C12N 15/70 | (2006.01) |
| C12N 15/74 | (2006.01) |

(52) U.S. Cl. .................. 424/93.2; 424/93.6; 435/320.1
(58) Field of Classification Search ............... 435/91.3, 435/320.1; 514/44
See application file for complete search history.

(56) References Cited

U.S. PATENT DOCUMENTS

| | | | |
|---|---|---|---|
| 4,980,286 A | 12/1990 | Morgan et al. | |
| 5,354,678 A | 10/1994 | Lebkowski et al. | |
| 5,585,362 A | 12/1996 | Wilson et al. | |
| 5,589,377 A | 12/1996 | Lebkowski et al. | |
| 5,616,326 A | 4/1997 | Spibey | |
| 5,670,488 A | 9/1997 | Gregory et al. | |
| 5,700,470 A | 12/1997 | Saito et al. | |
| 5,731,172 A | 3/1998 | Saito et al. | |
| 5,747,072 A | 5/1998 | Davidson et al. | |
| 5,756,283 A | 5/1998 | Wilson et al. | |
| 5,789,390 A | 8/1998 | Descamps et al. | |
| 5,820,868 A | 10/1998 | Mittal et al. | |
| 5,837,484 A | 11/1998 | Trempe et al. | |
| 5,843,742 A | 12/1998 | Natsoulis et al. | |
| 5,851,806 A | 12/1998 | Kovesdi et al. | |
| 5,858,351 A | 1/1999 | Podsakoff et al. | |
| 5,869,037 A | 2/1999 | Crystal et al. | |
| 5,871,982 A | 2/1999 | Wilson et al. | |
| 5,877,011 A | 3/1999 | Armentano et al. | |
| 5,885,808 A | 3/1999 | Spooner et al. | |
| 5,891,690 A | 4/1999 | Massie | |
| 5,919,676 A | 7/1999 | Graham et al. | |
| 5,922,576 A | 7/1999 | He et al. | |
| 5,928,944 A | 7/1999 | Seth et al. | |
| 5,932,210 A | 8/1999 | Gregory et al. | |
| 5,952,221 A | 9/1999 | Kurtzman et al. | |
| 5,962,311 A | 10/1999 | Wickham et al. | |
| 5,962,313 A | 10/1999 | Podsakoff et al. | |
| 5,998,205 A | 12/1999 | Hallenbeck et al. | |
| 6,013,487 A * | 1/2000 | Mitchell | ..................... 435/91.3 |
| 6,083,702 A * | 7/2000 | Mitchell et al. | ............... 435/6 |
| 6,280,978 B1 | 8/2001 | Mitchell et al. | |
| 2002/0115207 A1 | 8/2002 | Mitchell et al. | |

OTHER PUBLICATIONS

Somia and Verma, 2000, Nature Reviews: Genetics, 1:91-99.*
Heise et al., 1999, Cancer Research, 59: 2623-2628.*
Platt, 1998, Nature, 392 supplement: 11-17.*
Gage, 1998, Nature, 392 supplement, pp. 18-24.*
Fisher, 1997, Neurobiology of Disease, 4: 1-22.*
Wada et al., 2000, PNAS, 97: 10954-10959.*
Puttaraju et al., 1999, Nature Biotechnology, 17: 246-252.*
Rochlitz, 2001, Swiss Med Wkly, 131: 4-9.*
Bhaumik et al., 2004, PNAS, 101: 8693-8698.*
U.S. Appl. No. 10/693,192, filed Oct. 23, 2003, "Screening method for identification of efficient pre-trans-splicing molecules," Mitchell et al.
U.S. Appl. No. 10/374,784, filed Feb. 25, 2003, "Trans-splicing mediated imaging of gene expression," Mitchell et al.
U.S. Appl. No. 10/360,787, filed Jun. 5, 2002, "Spliceosome mediated RNA trans-splicing for correction of factor VIII genetic defects," Mitchell et al.
U.S. Appl. No. 10/198,447, filed Jul. 17, 2002, "Spliceosome mediated RNA trans-splicing for correction of skin disorders," Mitchell et al.

(Continued)

Primary Examiner—Anne M. Wehbe
Assistant Examiner—Joanne Hama
(74) Attorney, Agent, or Firm—Arent Fox PLLC

(57) ABSTRACT

The present invention provides methods and compositions for conferring tumor selective cell death on cancer cells expressing specific target precursor messenger RNA molecules (cancer cell selective target pre-mRNAs). The compositions of the invention include conditionally replicative adenoviruses that have been genetically engineered to express one or more pre-trans-splicing molecules (PTMs) designed to interact with one or more cancer cell target pre-mRNA and mediate a trans-splicing reaction resulting in the generation of novel chimeric RNA molecules (chimeric RNA) capable of encoding adenovirus specific protein(s). Adenovirus specific proteins include those proteins complementing an essential activity necessary for replication of a defective adenovirus. The methods and compositions of the invention may be used to target a lytic adenovirus infection to cancer cells thereby providing a method for selective destruction of cancer cells. In addition, the adenoviruses of the invention may be engineered to encode PTMs designed to interact with target pre-mRNAs encoded by infectious agents within a cell, thereby targeting selective destruction of cells infected with such agents.

14 Claims, 3 Drawing Sheets

OTHER PUBLICATIONS

Figure 1:
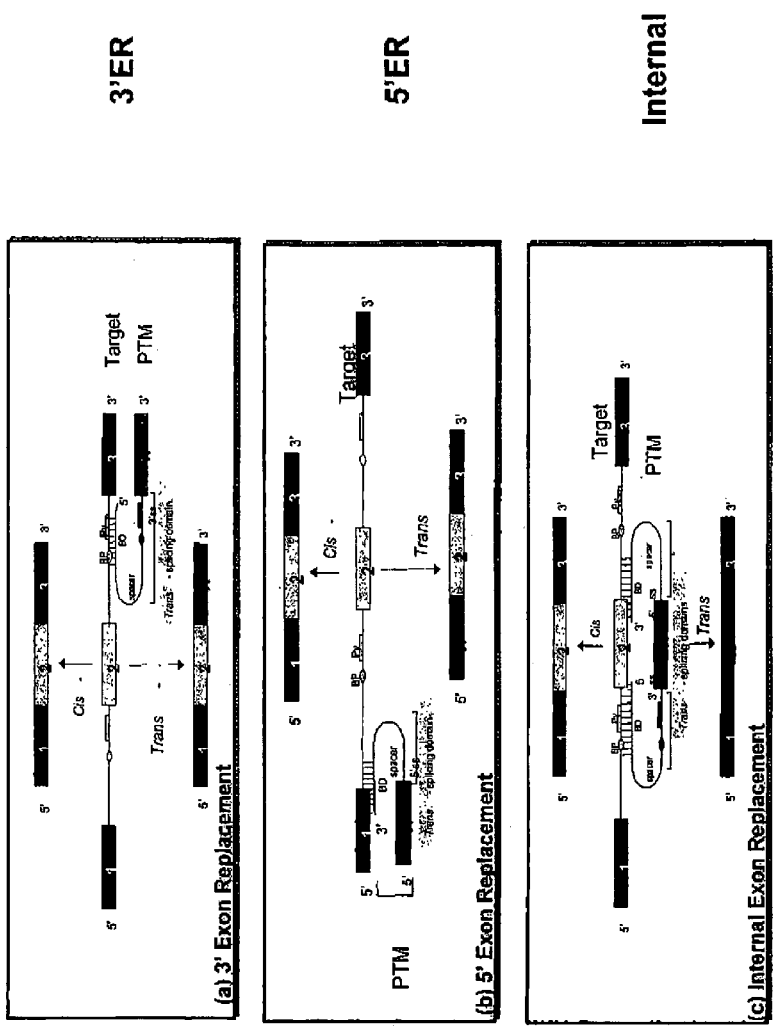

U.S. Appl. No. 10/136,723, filed Apr. 30, 2002, "Transgenic animal model for spliceosome-mediated RNA trans-splicing," Puttaraju et al.
U.S. Appl. No. 10/103,294, filed Mar. 30, 2002, "Spliceosome mediated RNA trans-splicing," Mitchell et al.
U.S. Appl. No. 10/075,028, filed Mar. 12, 2002, "Method and compositions for use in spliceosome mediated RNA trans-splicing," Mitchell et al.
U.S. Appl. No. 10/076,248, filed Feb. 12, 2002, "Method and compositions for use in spliceosome mediated RNA trans-splicing," Mitchell et al.
U.S. Appl. No. 10/941,492, filed Aug. 29, 2001, "Method and compositions for use in spliceosome mediated RNA trans-splicing," Mitchell et al.
U.S. Appl. No. 09/838,858, filed Apr. 20, 2001, "Method and compositions for use in spliceosome mediated RNA trans-splicing," Mitchell et al.
U.S. Appl. No. 09/756,097, filed Jan. 8, 2001, "Method and compositions for use in spliceosome mediated RNA trans-splicing," Mitchell et al.
U.S. Appl. No. 09/756,096, filed Jan. 8, 2001, "Methods and compositions for use on spliceosome mediated RNA trans-splicing," Mitchell et al.
Bhaumik et al., 2004, "Molecular Imaging of Gene Expression in Living Subjects by Spliceosome-Mediated RNA Trans-Splicing," Proc. Natl. Acad. Sci. USA, 101:8693-8698.
Tahara et al., 2004, "Trans-Splicing Repair of CD40-Ligand Deficiency Results in Naturally Regulated Correction of a Mouse Model of Hyper-IgM X-Linked Immunodeficiency," Nature Medicine, 10:835-841.
Chao et al., 2003, "Phenotype correction of Hemophilia A Mice by Spliceosome-Mediated RNA Trans-splicing," Nature Medicine, 9:1-5.
Liu et al., 2002, "Partial Correction of Endogenous Delta 508 CFTR in Human Cystic Fibrosis Airway Epithelia by Spliceosome-Mediated RNA Trans-Splicing," Nature Biotechnology, 20:47-52.
Kim et al., 2001,"Role of the Nonsense-Mediated Decay Factor hUpf3 in the Splicing Dependent Exon—Exon Junction Complex," Science 293:1832-1836.
Kirn et al., 2001, Replication-selective virotherapy for cancer:Biological principles, risk management and future directions, Nat. Med. 7:781-787.
Tian et al., 2001, "Strong RNA Splicing Enhancers Identified by a Modified Method of Cycled Selection Interact with SR Protein," J. Biological Chemistry 276:33833-33839.
Mansfield et al., 2000, "Repair of CFTR mRNA by spliceosome-mediated RNA trans-splicing," Gene Therapy 7:1885-1895.
Tacke et al., 1999, "Determinants of SR protein specificity," Curr. Opin. Cell Biol. 11:358-362.
He et al. 1998, "A Simplified System for Generating Recombinant Adenoviruses," Proc. Natl. Acad. Sci. USA, 95, 2509-2514.
Lan N et al., 1998, "Ribozyme-mediated Repair of Sickle β-Globin mRNAs in Erythrocyte Precursors" Science 280:1593-1596.
Phylactou LA et al., 1998, "Ribozyme-mediated trans-splicing of a trinucleotide repeat" Nature Genetics 18:378-381.
Staley JP et al., 1998, "Mechanical Devices of the Spliceosome: Motors, Clocks, Springs and Things" Cell 92:315-326.
Bellet et al., 1997, "Malignant transformation of nontrophoblastic cells is associated with the expression of chorionic gonadotropin β genes normally transcribed introphoblastic cells," Cancer Res. 57:516.
Coolidge et al., 1997, "Functional analysis of the polypyrimidine tract in pre-mRNA splicing," Nucleic Acids Res. 25:888.
Crouzet et al. 1997, "Recombinational Construction in *Escherichia coli* of Infectious Adenoviral Genomes," Proc. Natl. Acad. Sci. USA, 94, 1414-1419.
Good et al., 1997, "Expression of Small, Therapeutic RNAs in Human Cell Nuclei," Gene Ther. 4:45-54.
Malek O et al., 1997, "Evolution of trans-splicing plant mitochondrial introns in pre-Permian times" Proc. Nat'l Acad. Sci. USA 94:553-558.
Chartier, et al. 1996, "Efficient Generation of REcombinant Adenovirus Vectors by Homologous Recombination in *Escherichia coli*," J Virol. 70, 4805-4810.
Hoon et al., 1996, "Detection of metastatic breast cancer by β-hCG polymerase chain reaction," Int J. Cancer 69:369.
Jones JT et al., 1996, "Tagging ribozyme reaction sites to follow trans-splicing in mammalian cells" Nature Medicine 2:643-648.
Krämer A, 1996, "The structure and function of proteins involved in mammalian Pre-mRNA splicing" Annu. Rev. Biochem. 65:367-404.
Miyake et al. 1996, "Efficient Generation of Recombinant Adenoviruses Using Adenovirus DNA-Terminal Protein Complex and A Cosmid Bearing the Full-Length Virus Genome," Proc. Natl. Acad. Sci. USA, 93, 1320-1324.
Nilsson J et al., 1996, "Multiple affinity domains for the detection, purification, and immobilization of recombinant proteins," J. Mol. Recognit., 1996, 5:585-594.
Pasman Z et al., 1996, "The 5' and 3' splice sites come together via a three dimensional diffusion mechanism" Nucleic Acids Res. 24(9):1638-1645.
Boelens et al., "Nuclear Retention of RNA as a Mechanism," 1995 RNA 1:273-83.
Bruzik JP et al., 1995, "Enhancer-dependent interaction between 5' and 3' splice sites in trans" Proc. Nat'l. Acad. Sci. USA 92:7056-7059.
Chiara MD et al., 1995, "A two-step mechanism for 5' and 3' splice-site pairing" Nature 375:510-513.
Davis RE et al., 1995, "RNA Trans-splicing in Flatworms" J. Biol. Chem. 270:21813-21819.
Eul J et al., 1995, Experimental evidence for RNA trans-splicing in mammalian cells: EMBO. J. 14(13):3226-3235.
Fu, 1995, "The Superfamily of Arginine/Serine-Rich Splicing Factors," RNA 1:663-680.
Bett et al. 1994, "An Efficient and Flexible System for Construction if Adenovirus Vectors with Insertions or Deletions in Early Regions 1 and 3," Proc. Natl. Acad. Sci. USA, 91,8802-6.
Hollenberg et al., 1994, "Multiple promoter elements in the human chorionic gonadotropin b subunit genes distinguish their expression from luteinizing hormone β gene," Mol. Cell Endo., 106:111-119.
Ketner et al. 1994, "Efficient manipulation of the Human Adenovirus Genome as an Infectious Yeast Artificial Chromosome Clone," Proc. Natl. Acad. Sci. USA, 91, 6186-6190.
Sullenger BA et al., 1994, "Ribozyme-mediated repair of defective mRNA by targeted trans-splicing" Nature 341:619-622.
Goldspiel et al., 1993, "Human gene therapy," Clinical Pharmacy 12:488-505.
Kozarsky and Wilson, 1993, "Gene therapy:adenovirus vectors," Current Opinion in Genetics and Development 3:499-503.
Miller et al., 1993, "Use of adenoviral vectors for gene transfer and expression," Meth. Enzymol. 217:581-599.
Moore and Sharp, 1993, "Evidence for two active sites in the spliceosome provided by stereochemistry of pre-mRNA splicing," Nature, 365:364-368.
Moore, 1993, "Splicing of precursors to mRNA by the spliceosome," in RNA World, R.F. Gesteland and J.F. Atkins, eds. Cold Spring Harbor Laboratory Press, 303-358.
Morgan and Anderson, 1993, "Human Gene Therapy," Ann. Rev. Biochem. 62:191-217.
Mulligan, 1993, "The basic science of gene therapy," Science 260:926-932.
Roscigno et al., 1993, "A mutational analysis of the polypyrimidine tract of introns," J. Bio. Chem., 268:11222-11229.
Tolstoshev, 1993, "Gene therapy, concepts, current trials, and future directions," Ann. Rev. Pharmacol. Toxicol. 33:573-596.
Acevedo et al., 1992, "Human chorionic gonadotropin-beta subunit gene expression in cultured human fetal and cancer cells of different types and origins," Cancer 76:1467.
Bruzik JP et al., 1992, "Spliced leader RNAs from lower eukaryotes are trans-spliced in mammalian cells," Nature 360:692-695.
Vellard M et al., 1992, "A potential splicing factor is encoded by the opposite strand of the trans-spliced c-myb exon" Proc. Nat'l. Acad. Sci., 89:2511-2515.

Dingwall and Laskey, 1991, "Nuclear Targeting Sequences—A Consensus?" Trends in Biochem. Sci. 16:478-481.
Ghattas et al., 1991, "The Encephalomyocarditis Virus Internal Ribosome Entry Site Allows Efficient Coexpression of Two Genes from a Recombinant Provirus in Culture Cells and in Embryos," Mol. Cell Biol. 11:5848-5859.
Jankrecht et al., 1991, "Rapid and efficient purification of native histidine-tagged protein expressed by recombinant vaccinia virus," Proc. Natl. Acad. Sci., 88:8972-8976.
Rosenfeld et al. 1991, "Adenovirus-Mediated Transfer of a Recombinant α-1 Antitrypsin Gene to the Lung Epithelium in Vivo," Science. 252, 431-4.
Wu and Wu, 1991, "Delivery systems for gene therapy," Biotherapy 3:87-95.
Rajkovic A et al., 1990, "A spliced leader is present on a subset of mRNAs from the human parasite *Schistosoma mansoni*" Proc. Nat'l. Acad. Sci. USA, 87:8879-8883.
Schneider et al., 1990, "Building blocks for oligonucleotide analogs with dimethyl-sulfide-sulfoxide and sulfone groups replacing phosphodiester linkages," Tet. Letters, 31:335-338.
Senapathy et al., 1990, "Splice junctions, branch point sites, and exons:sequence statistics, identification, and applications to genome project," Methods of Enzymology, 183:252-278.
Uhlmann et al., 1990, "Antisense Oligonucleotides: A New Therapeutic Principle," Chemical Reviews, 90:543-584.
International Patent Application No. PCT/US89/01589, published on Nov. 2, 1989 as International Publication No. WO89/10134.
Kerem et al., 1989, "Identification of the Cystic Fibrosis Gene: Genetic analysis," Science, 245:1073-1080.
Letsinger et al., 1989, "Cholesterol-conjugated oligonucleotides;synthesis, properties and activity as inhibitors of replication of human immunodeficiency virus in cell culture," Proc. Natl. Acad. Sci., 86:6553-6556.
Reed, 1989, "The organization of 3' splice sites sequences in mammalian introns," Genes Dev. 3:2113.
Riordan et al., 1989, "Identification of the Cystic Fibrosis Gene:Cloning and characterization of complementary DNA," Science, 245:1066-1073.
Rommens et al., 1989, "Identification of the Cystic Fibrosis Gene: Chromosome walking and jumping," Science, 245:1059-1065.
Shimizu A et al., 1989, "Immunoglobulin double-isotype expression by trans-mRNA in a human immunoglobulin transgenic mouse" Proc. Nat'l. Acad. Sci. USA 86:8020-8023.
Smith et al., 1989, "Scanning from an independently specified branch point defines the 3' splice site of mammalian introns," Nature, 342:243-247.
International Patent Application No. PCT/US88/02009 of Synthetic Genetics, published on Dec. 15, 1988 as International Publication No. WO88/09810.
van der Krol et al., 1988, "Modulation of eukaryotic gene expression by complementary RNA or DNA sequences," BioTechniques, 6:958-976.
Reed & Maniatis 1988, "The role of the mammalian branchpoint sequence in the pre-mRNA splicing," Genes Dev. 2:1268.
Smith et al, 1988, "Single-step purification of polypepetides expressed in *Escherichia coli* as fusions with glutathione S-transferase," Gene, 67:31.
Zon et al., 1988, "Oligonucleotide analogues as potential chemotherapeutic agents," Pharm. Res., 5:539-549.
Krause M et al., 1987, "A Trans-spliced Leader Sequence on Actin mRNA in C. elegans" Cell 49:753-761.

Lemaitre et al., 1987, "Specific antiviral activity of a poly(L-lysine)-conjugated oligodeoxyribonucleotide sequence complementary to vesicular stomatitis virus N protein mRNA initiation site," Proc. Natl. Acad. Sci., 84:648-652.
Dingwall and Laskey, 1986, "Protein Import into the Cell Nucleus," Ann. Rev. Cell Biol. 2:367-390.
Murphy et al., 1986, "Identification of a novel Y branch structure as an intermediate in Trypanosome m RNA processing:evidence for Trans splicing," Cell, 47:517.
Smith et al., 1986, "Mr 26,000 antigen of *Schistosoma japonica* recognized by resistant WEH1 129/J mice is a parasite glutathione S-transferase," Proc. Natl. Acad. Sci., 83:8703-8707.
Sutton RE et al., 1986, "Evidence for Trans Splicing in Trypanosomes" Cell 47:527-535.
Konarska MM et al., 1985, "Trans Splicing of mRNA Precursors In Vitro" Cell 46:165-171.
Solnick D, 1985, "Trans Splicing of mRNA Precursors" Cell 42:157-164.
Talmadge et al., 1984, "Only three of the seven chorionic gonadotropin beta subunit genes can be expressed in the placenta," Nucleic Acids Res. 12:8415.
Accession No. K01722, Corynebacteriophage beta diptheria toxin (DT) gene, 1983.
Berkner, et al. 1983, "Generation of Adenovirus by Transfection of Plasmids," Nucleic Acids Res. 11, 6003-6020.
Greenfield, 1983, "Nucleotide sequence of the structural gene for the diptheria toxin carried by corynebacteriophage β," Proc. Natl. Acad. Sci., 80:6853-6857.
Brinster et al., 1982, "Regulation of metallothionein-thymidine kinase fusion plasmids injected into mouse eggs," Nature, 296:39-42.
Benoist et al., 1981, "In vivo sequence requirements of the SV40 early promoter region," Nature, 290:304-310.
Wagner TE et al., 1981, "Microinjection of a rabbit β-globin gene into zygotes and its subsequent expression in adult mice and their offspring" Proc. Natl. Acad. Sci. USA 78(10):6376-6380.
Yamamoto et al., 1980, "Identification of a functional promoter in the long terminal repeat of Rous Sarcoma Virus," Cell, 22:39-42.
Berget SM et al., 1977, "Spliced segments at the 5' terminus of adenovirus 2 late mRNA" Proc. Natl. Acad. Sci. USA 74(8):3171-3175.
Chow LT et al., 1977, "An Amazing Sequence Arrangement at the 5' Ends of Adenovirus 2 Messenger RNA" Cell 12:1-8.
Graham et al., 1977, "Characteristics of a Human Cell Line Transformed by DNA from Human Adenovirus Type 5," J. Gen. Virol. 36:59-72.
Uchida et al, 1973, "Diptheria toxin and related proteins: isolation and properties of mutant proteins related to diptheria toxin," J. Biol. Chem., 248:3838.
Puttaraju, et al., *Spliceosome-mediated RNA trans-splicing as a tool for gene therapy,* 1999 Nature America Inc., vol. 17, pp. 246-252.
Wu et al., *Receptor-mediated in Vitro Gene Transformatin by a Soluble DNA Carrier System,* The Journal of Biological Chemistry, vol. 262, No. 10, Issue of Apr. 5, pp. 4429-4432, 1987.
Gilardi et al., *Expression of human α₁-antitrypsin using a recombinant adenovirus vector,* Elsevier Science Publishers B.V., vol. 267, No. 1, pp. 60-62, 1990.
Moore et al., *Splicing of Precursors to mRNA by the Spliceosome,* The RNA World, pp. 303-357 1993.

* cited by examiner

USE OF SPLICEOSOME MEDIATED RNA TRANS-SPLICING TO CONFER CELL SELECTIVE REPLICATION TO ADENOVIRUSES

This application claims the benefit of U.S. Provisional Application No. 60/378,690, filed May 8, 2002.

1. INTRODUCTION

The present invention provides methods and compositions for conferring selective adenovirus mediated cell death on cells expressing a specific target precursor messenger RNA (selective target pre-mRNAs). The compositions of the invention include conditionally replicative adenoviruses that have been genetically engineered to express one or more pre-trans-splicing molecules (PTMs) designed to interact with one or more selective target pre-mRNA and mediate a trans-splicing reaction resulting in the generation of novel chimeric RNA molecules (chimeric RNA) capable of encoding an adenovirus specific protein(s). Adenovirus specific proteins include those proteins complementing an essential activity necessary for replication of conditionally replicative adenoviruses. Upon successful trans-splicing between the target pre-mRNA and the PTM, the adenovirus peptide(s) are expressed thereby providing the required complementing activity necessary for replication of the conditionally replicative adenoviruses. Such viral replication leads to cell lysis, thereby targeting selective destruction of infected cells.

The methods and compositions of the invention may be used to treat a variety of different diseases where the goal is selective destruction of a specific cell type. For example, the present invention provides methods and compositions for conferring selective cell death on cancer cells expressing a specific target precursor messenger RNA molecules (cancer cell selective target pre-mRNAs). Such compositions include conditionally replicative adenoviruses that have been genetically engineered to express one or more pre-trans-splicing molecules (PTMs) designed to interact with one or more cancer cell selective target pre-mRNA and mediate a trans-splicing reaction resulting in the generation of novel chimeric RNA molecules (chimeric RNA) capable of encoding an adenovirus specific protein(s). Alternatively, the present invention may be utilized to confer selective cell death on cells infected with a pathogenic microorganism. In such instances, conditionally replicative adenoviruses are engineered to encode PTMs designed to interact with one or more target pre-mRNA encoded by the pathogenic microorganism, or induced within the cells of a subject infected with a pathogenic microorganism and encode an adenovirus polypeptide(s). Upon successful trans-splicing between the target pre-mRNA and the PTM, the adenovirus peptide(s) are expressed thereby providing the required complementing activity necessary for replication of the conditionally replicative adenoviruses.

2. BACKGROUND OF THE INVENTION

2.1. Trans-Splicing

DNA sequences in the chromosome are transcribed into pre-mRNAs which contain coding regions (exons) and generally also contain intervening non-coding regions (introns). Introns are removed from pre-mRNAs in a precise process referred to as splicing. In most cases, the splicing reaction occurs within the same pre-mRNA molecule, which is termed cis-splicing. Splicing between two independently transcribed pre-mRNAs is termed trans-splicing. Trans-splicing was first discovered in trypanosomes (Sutton & Boothroyd, 1986, Cell 47:527; Murphy et al., 1986, Cell 47:517) and subsequently in nematodes (Krause & Hirsh, 1987, Cell 49:753); flatworms (Rajkovic et al., 1990, Proc. Nat'l. Acad. Sci. USA, 87:8879; Davis et al., 1995, J. Biol. Chem. 270:21813) and in plant mitochondria (Malek et al., 1997, Proc. Nat'l. Acad. Sci. USA, 94:553). In the parasite *Trypanosoma brucei*, all mRNAs acquire a splice leader (SL) RNA at their 5' termini by trans-splicing. A 5' leader sequence is also trans-spliced onto some genes in *Caenorhabditis elegans*. This mechanism is appropriate for adding a single common sequence to many different transcripts.

U.S. Pat. Nos. 6,083,702, 6,013,487 and 6,280,978 describe the use of pre-trans-splicing molecules (PTMs) to mediate a trans-splicing reaction by contacting a target precursor mRNA to generate novel chimeric RNAs. The resulting RNA can encode any gene product including a protein of therapeutic value to the cell or host organism, a toxin, such as Diptheria toxin subunit A, which causes killing of the specific cells or a novel protein not normally present in cells. The PTMs can also be engineered for the identification of exon/intron boundaries of pre-mRNA molecules using an exon tagging method and for production of chimeric proteins including those encoding peptide affinity purification tags which can be used to purify and identify proteins expressed in a specific cell type.

2.2. Adenovirus Based Gene Therapy

Gene therapy has recently been developed as a method for delivering genetic information into some or all the cells of a host. The genetic information may be in the form of a gene or a derivative of a gene, such as a cDNA capable of encoding a protein. Applications of gene therapy include the treatment of genetic disorders by providing a protein which is absent or mutated in the host, the treatment of tumors or other acquired diseases.

For purposes of gene therapy, one difficulty has been the successful delivery of genetic information to the target cells. For example, a major difficulty in the field of cancer gene therapy has been the inability to deliver replication-defective vectors to enough cancer cells to provide a therapeutic benefit. One method that has been recently developed is the use of viral vectors engineered to express the genetic information of interest. Gene delivery vectors derived from adenoviruses have a number of features that make them particularly useful for gene therapy. For example, adenoviruses have been extensively studied and are not known to be associated with any serious pathology, do not integrate into the genome, the virus is able to replicate in non-proliferating cells, they have a broad host-range, and the virus can be rendered replication defective by deletion of one or more of the early-region genes of the virus. Vectors derived from adenoviruses where one or more of the early region genes has been deleted and replaced by a gene of interest have been previously used for gene therapy experiments in the clinical and pre-clinical phase. Such recombinant viruses are rendered defective due to deletion of a portion of the viral genome. However, in such instances the rescue of the replication defective virus can be achieved by providing in trans the missing adenovirus gene products, i.e., complementation.

Tumor-selective promoters have been used to replace early gene promoters in adenoviruses, and these adenoviruses have been shown to preferentially replicate in and kill cancer cells (U.S. Pat. No. 5,998,205; Kirn et al., 2001, Nat. Med. 7:781–787). The degree of tumor selectivity of early gene expression and adenoviral replication varies depending on the choice of the tumor promoter used. In many cases, the promoter does not provide tight enough control, thereby resulting in toxicity from adenoviral replication in normal cells. Another problem associated with the use of such vectors is that there is a physical constraint on the size and number of tumor selective promoters that can be inserted into the adenoviral genome. The genome of wildtype adenovirus is 36 kilobases (kb) and genomes larger than approximately 38 kb package poorly.

The present invention provides methods and compositions for conferring selective cell death on cells expressing specific target precursor messenger RNA molecules. Specifically, the invention provides recombinant conditionally replicative adenoviruses that have been engineered to express PTM molecules that are designed to interact with one or more cell selective target pre-mRNA and mediate trans-splicing reactions resulting in the generation of chimeric RNA molecules capable of encoding an adenovirus protein(s). The expression of the adenovirus protein(s) permits replication of the conditionally replicative adenovirus leading to lysis of the selected cell. The present invention provides a system for targeting cancer cell destruction that does not rely on the use of tumor specific promoters. In addition, the invention provides a system for targeting selective cell death to cells infected with pathogenic microorganisms, or, cell death in instances where the activity of a particular cell type leads to disease.

3. SUMMARY OF THE INVENTION

The present invention provides methods and compositions for conferring selective adenovirus mediated cell death on cells expressing a specific target precursor messenger RNA (selective target pre-mRNAs). The compositions of the invention include conditionally replicative adenoviruses that have been genetically engineered to express one or more pre-trans-splicing molecules (PTMs) designed to interact with one or more selective target pre-mRNA and mediate a trans-splicing reaction resulting in the generation of novel chimeric RNA molecules (chimeric RNA) capable of encoding an adenovirus specific protein(s). Adenovirus specific proteins include those proteins complementing an essential activity necessary for replication of conditionally replicative adenoviruses. Upon successful trans-splicing between the target pre-mRNA and the PTM, the adenovirus peptide(s) are expressed thereby providing the required complementing activity necessary for replication of the conditionally replicative adenoviruses. Such viral replication leads to cell lysis, thereby targeting selective destruction of infected cells.

The present invention provides methods and compositions for conferring tumor selective cell death on cancer cells expressing specific target precursor messenger RNA molecules (cancer cell selective target pre-mRNAs). The compositions of the invention include conditionally replicative adenoviruses that have been genetically engineered to express pre-trans-splicing molecules (PTMs) designed to interact with one or more cancer cell selective target pre-mRNA and mediate trans-splicing reactions resulting in the generation of novel chimeric RNA molecules (chimeric RNA) capable of encoding an adenovirus specific protein(s). The portion of the target pre-mRNA trans-spliced to the PTM provides the signal sequences necessary for initiation of translation of the chimeric RNA molecule. The portion of the PTM trans-spliced to the target pre-mRNA provides sequences encoding adenovirus specific proteins that provide essential activity necessary for complementation of the conditionally replicative adenoviruses.

The methods and compositions of the invention provide a means for generating a self-amplifying cytotoxic agent, e.g., the adenovirus, which is able to spread throughout the tumor thereby providing a method for selective destruction of cancer cells within the tumor. Thus, the present invention provides methods and compositions for treating a variety of different cancers including but not limited to, breast, prostate, bladder, pancreatic or liver cancer.

In addition the present invention provides methods and compositions for conferring selective cell death on cells expressing mRNAs produced by a pathogenic infectious agent. In such instances the PTM is designed to interact with one or more target pre-mRNAs produced by the pathogenic infective agent. The portion of the target pre-mRNA produced by the pathogen and trans-spliced to the PTM provides the signal sequences necessary for initiation of translation of the chimeric molecule. The portion of the PTM trans-spliced to the target pre-mRNA provides sequences encoding the adenovirus specific proteins that provide an essential activity necessary for complementation of the conditionally replicative adenovirus. The methods and compositions of the invention may be utilized for selective destruction of infected cells.

In yet another embodiment of the invention, recombinant adenoviruses may be used for conferring cell death in a subject where the activity of that cell leads to a disease state, for example, an immune or hormonal disorder.

Further, the present invention provides methods and compositions for conferring the ability to express a therapeutic or diagnostic polypeptide on a cell expressing a selective pre-mRNA. For example, the conditionally replicative viruses may be engineered to express PTMs capable of encoding a therapeutic or diagnostic polypeptide upon trans-splicing to a selective pre-mRNA. The diagnostic or therapeutic polypeptides may be expressed independently, or alternatively, may be expressed as adenovirus fusion proteins. Adenoviruses expressing therapeutic polypeptides may be used to target treatment to a specific cell type or tissue, while, adenoviruses expressing diagnostic polypeptides may be used to detect cells expressing the target pre-mRNA, for example, through imaging.

4. BRIEF DESCRIPTION OF THE DRAWINGS

FIG. 1. Schematic representation of different trans-splicing reactions. (a) trans-splicing reactions between the target 5' splice site and a PTM 3' splice site; (b) trans-splicing reactions between the target 3' splice site and a PTM 5' splice site; (c) replacement of internal exon by double trans-splicing reaction in which the PTM carries both 5' and 3' splice sites. BD, binding domain, BP, branchpoint sequence, PPT, polypyrimidine tract and ss, splice site.

Figure 2:
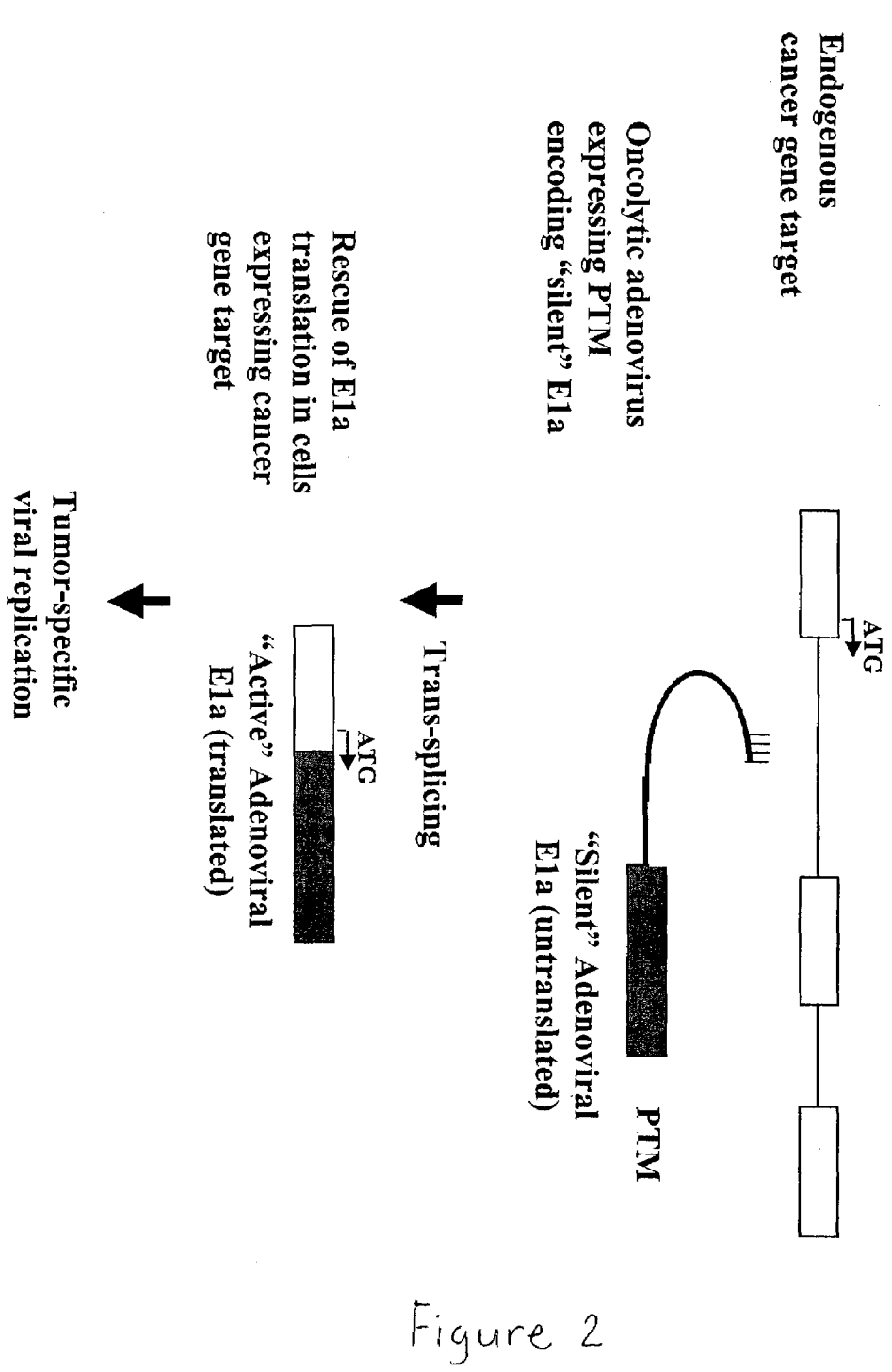

FIG. 2. Schematic representation of adenoviruses as anti-cancer agents.

Figure 3:
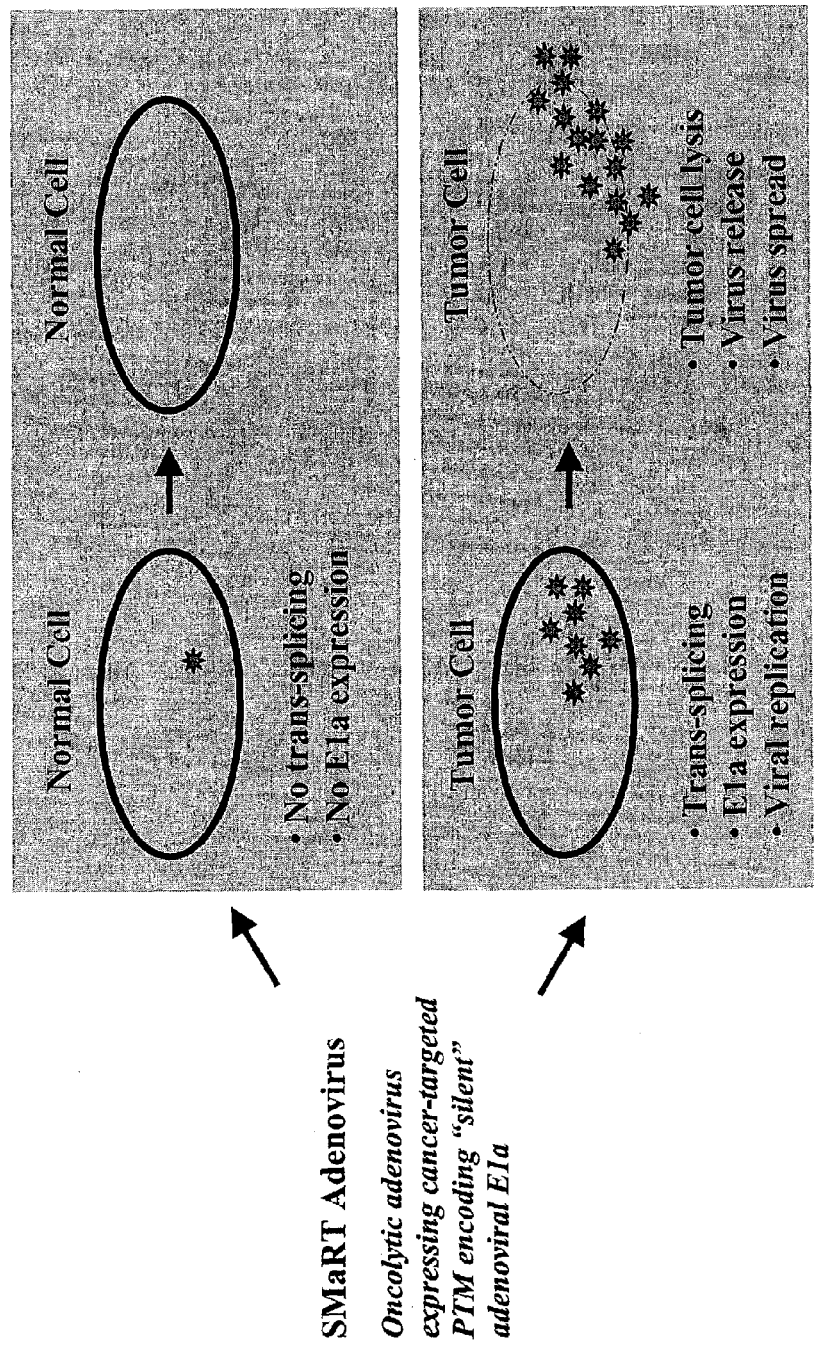

FIG. 3. Schematic diagrams of PTM-mediated control of adenoviral replication.

5. DETAILED DESCRIPTION OF THE INVENTION

The present invention provides methods and compositions for conferring adenovirus mediated cell death on cells expressing a specific target precursor messenger RNA molecules. The target precursor messenger RNA molecules may be selectively expressed in cancer cells, or alternatively, the RNA molecules may be those encoded by infectious agents such as bacteria, parasites, fungi or viruses. Target pre-mRNAs also include those cellular pre-mRNAs induced during bacterial, parasitic, fungal or viral infection, or, pre-mRNAs wherein expression of said pre-mRNA is associated with a specific disease or disorder. The compositions of the invention include, for example, recombinant adenoviruses that have been genetically engineered to express pre-trans-splicing molecules (PTMs) designed to interact with one or more cancer cell selective target pre-mRNAs, or target pre-mRNAs encoded by an infectious agent and mediate trans-splicing reactions resulting in the generation of a novel chimeric RNA molecules (chimeric RNA) encoding adenovirus specific protein(s) capable of rescuing the conditionally replicative adenovirus. Specifically, the PTMs of the invention are designed to encode adenovirus specific proteins that are required for replication of conditionally replicative adenovirus thereby providing for complementation of said adenovirus. The methods and compositions of the invention may be used to target a lytic adenovirus infection to cancer cells or cells infected with a pathogenic agent thereby providing a method for selective destruction of cancer cells or cells infected with an infectious agent. In addition, the recombinant adenoviruses may be designed to express PTM molecules that encode for diagnostic or therapeutic polypeptides. The polypeptides may be expressed independently, or alternatively, as adenovirus fusion proteins. Such recombinant conditionally replicative adenoviruses permit targeting of a therapeutic or diagnostic polypeptide to a cell expressing a selective pre-mRNA.

5.1. Structure of the Pre-Trans-Splicing Molecules

The compositions of the invention include recombinant conditionally replicative adenoviruses that have been genetically engineered to express one or more PTMs designed to interact with one or more selective target pre-mRNA molecule such as, for example, cancer cell selective target pre-mRNA, target pre-mRNA molecules encoded by an infectious agent, target cellular pre-mRNAs induced by an infectious microorganism, or target pre-mRNAs where the expression of said pre-mRNA is associated with a disease or disorder. Such RNAs are designed to mediate trans-splicing reactions resulting in the generation of novel chimeric RNA molecules (chimeric RNAs). The novel chimeric RNA is designed to encode a complementing adenovirus protein(s) capable of rescuing the defect of the conditionally replicative adenovirus. Such rescue leads to a lytic adenovirus infection resulting in cell lysis. The compositions of the invention provide a means for conferring selective adenovirus mediated cell death on cells expressing a specific target pre-mRNA. The conditionally replicative adenoviruses of the invention are designed to encode PTMs comprising (i) one or more target binding domains that targets binding of the PTM to a specific pre-mRNA target (ii) a 3' splice region that includes a 3' splice acceptor site and/or 5' splice donor site; and (iii) a nucleotide sequence capable of encoding at least one adenovirus protein necessary for replication of adenovirus. In addition to adenovirus proteins, the PTMs may include sequences capable of encoding diagnostic or therapeutic polypeptides. Such polypeptides may be expressed as adenovirus fusion proteins, wherein the adenovirus portion of the fusion protein retains its ability to provide complementing activity. Alternatively, PTMs may be engineered to independently express the diagnostic or therapeutic polypeptide.

In some instances, the PTMs of the invention may further comprise one or more spacer regions that separate the RNA splice site from the target binding domains and/or a safety sequence. The structure of PTMs is described in detail in U.S. Pat. Nos. 6,013,487, 6,083,702, 6,280,978, and in co-pending U.S. patent application Ser. Nos. 09/756,095, 09/756,096, 09/756,097 the disclosures of which are incorporated by reference herein.

The target-binding domain of the PTM may contain multiple binding domains which are complementary to and in anti-sense orientation to the targeted region of the target specific pre-mRNA, e.g., a cancer selective pre-mRNA or a pre-mRNA encoded by a pathogenic microorganism. As used herein, a target binding domain(s) is defined as any sequence that confers specificity of binding and anchors the pre-mRNA closely in space so that the spliceosome processing machinery of the nucleus can trans-splice a portion of the PTM to a portion of the pre-mRNA. The target binding domains may comprise up to several thousand nucleotides. In preferred embodiments of the invention the binding domains may comprise at least 10 to 30 and up to several hundred nucleotides. The specificity of the PTM may be increased significantly by increasing the length of the target binding domain. In addition, although the target binding domain may be "linear" it is understood that the RNA may fold to form secondary structures that may stabilize the complex by preventing activation of the PTM splice site until the binding domain has encountered its target thereby increasing the efficiency of splicing. Absolute complementarity with the cancer cell selective pre-mRNA, although preferred, is not required. A sequence "complementary" to a portion of an RNA, as referred to herein, means a sequence having sufficient complementarity to be able to hybridize with the RNA, forming a stable duplex. The ability to hybridize will depend on both the degree of complementarity and the length of the nucleic acid (See, for example, Sambrook et al., 1989, Molecular Cloning, A Laboratory Manual, 2d Ed., Cold Spring Harbor Laboratory Press, Cold Spring Harbor, N.Y.). Generally, the longer the hybridizing nucleic acid, the more base mismatches with an RNA it may contain and still form a stable duplex. One skilled in the art can ascertain a tolerable degree of mismatch or length of duplex by use of standard procedures to determine the stability of the hybridized complex.

In an embodiment of the invention, the target binding domain of the PTM will contain sequences which are complementary to and in anti-sense orientation to a cancer cell selective target pre-mRNA molecules where the goal is to target a lytic adenoviral infection to cancer cells thereby targeting cancer cell destruction. For example, PTM binding sites may be engineered to bind to any target pre-mRNA where the expression of the target pre-mRNA is associated with a proliferative disorder or disease. Such target pre-mRNAs are characterized as those pre-mRNAs expressed in cancer cells but which are either absent or expressed in low levels in their normal cell counterparts. Such target pre-mRNAs include, for example, the β-chorionic gonadotropin 6 pre-mRNA, the epidermal growth factor receptor pre-mRNA, E2F-1 pre mRNA or telomerase pre mRNA each of which are known to be over expressed in tumor cells and prostate specific G-protein coupled receptor (PSGR) pre-mRNA which is known to be over expressed in prostate cancer.

The methods and compositions of the present invention may be designed to target any pre-mRNA known to be differentially expressed in cancer cells but not normal cells. Additionally, techniques well known to those of skill in the art may be used to identify novel genes differentially expressed in cancer cells but not their normal counterpart. Such techniques includes, for example, the use of cDNA microarrays to identify differentially expressed genes in cancer cells. (See, Ausebel et al., 2003, Current Protocols in Molecular Biology, John Wiley & Sons, Inc., Chapter 25)

In yet another embodiment of the invention, the target binding domain of the PTM will contain sequences which are complementary to and in anti-sense orientation to specific target pre-mRNA molecules encoded by an infectious agent where the goal is to target a lytic adenoviral infection to cells infected with the agent thereby targeting infected cell destruction. For example, PTM binding sites may be engineered to bind to any target pre-mRNA where the expression of the target pre-mRNA is associated with a viral, bacterial, fungal or parasitic disease, for example.

Binding may also be achieved through other mechanisms, for example, through triple helix formation or protein/nucleic acid interactions such as those in which the PTM is engineered to recognize a specific RNA binding protein, e.g., a protein bound to a specific target pre-mRNA. Alternatively, the PTMs of the invention may be designed to recognize secondary structures, such as for example, hairpin structures resulting from intramolecular base pairing between nucleotides within an RNA molecule.

As indicated above, the PTM molecules of the invention are also designed to contain a 3' splice region that may include a branchpoint, pyrimidine tract and a 3' splice acceptor AG site and/or a 5' splice donor site. Consensus sequences for the 5' splice donor site and the 3' splice region used in RNA splicing are well known in the art (See, Moore, et al., 1993, The RNA World, Cold Spring Harbor Laboratory Press, p. 303–358). In addition, modified consensus sequences that maintain the ability to function as 5' donor splice sites and 3' splice regions may be used in the practice of the invention. Briefly, the 5' splice site consensus sequence is AG/GURAGU (where A=adenosine, U=uracil, G=guanine, C=cytosine, R=purine and/=the splice site). The 3' splice site consists of three separate sequence elements: the branchpoint or branch site, a polypyrimidine tract and the 3' consensus sequence (YAG). The branchpoint consensus sequence in mammals is YNYURAC (Y=pyrimidine). The underlined A is the site of branch formation. A polypyrimidine tract is located between the branchpoint and the splice site acceptor and is important for efficient branchpoint utilization and 3' splice site recognition.

Recently, pre-messenger RNA introns beginning with the dinucleotide AU and ending with the dinucleotide AC have been identified and referred to as U12 introns. U12 intron sequences as well as any sequences that function as splice acceptor/donor sequences may also be used in PTMs.

A spacer region to separate the RNA splice site from the target binding domain is may also be included in the PTM. The spacer region may have additional features such as sequences that enhance trans-splicing to the target pre-mRNA. In a specific embodiment of the invention, initiation codon(s) and pre-mature termination codons may be incorporated into the PTMs of the invention as a mechanism for targeting selective degradation of unspliced RNAs thereby preventing translation and expression of unspliced RNAs from the nucleus into the cytoplasm. (see, Kim et al., 2001 Science 293:1832–1836)

In a preferred embodiment of the invention, a "safety" is also incorporated into the spacer, binding domain, or elsewhere in the PTM to prevent non-specific trans-splicing. This is a region of the PTM that covers elements of the 3' and/or 5' splice site of the PTM by relatively weak complementarity, preventing non-specific trans-splicing. The PTM is designed in such a way that upon hybridization of the binding/targeting portion(s) of the PTM, the 3' and/or 5' splice site is uncovered and becomes fully active.

The "safety" consists of one or more complementary stretches of cis-sequence (or could be a second, separate, strand of nucleic acid) which weakly binds to one or both sides of the PTM branchpoint, pyrimidine tract, 3' splice site and/or 5' splice site (splicing elements), or could bind to parts of the splicing elements themselves. This "safety" binding prevents the splicing elements from being active (e.g., block U2 snRNP or other splicing factors from attaching to the PTM splice site recognition elements). The binding of the "safety" may be disrupted by the binding of the target binding region of the PTM to the target pre-mRNA, thus exposing and activating the PTM splicing elements (making them available to trans-splice into the target pre-mRNA).

The PTMs of the invention, further comprise a nucleotide sequence encoding an adenovirus polypeptide capable of complementing the conditionally replicative adenoviruses of the invention. Such adenoviral polypeptides preferably include those encoded by the adenovirus early regions. Three such regions, E1, E2, E4, are essential to viral replication. Thus, the PTMs of the invention are designed to encode, for example, adenovirus E1A, E1B, E2A, E2B or E4 polypeptides. In a preferred embodiment of the invention, the adenoviral proteins are derived from, for example, adenovirus types 2 5, 9 or 35. Nucleotide sequences encoding such adenoviral polypeptides are publicly available and are well known to those of skill in the art. Trans-splicing of a portion of the target pre-mRNA, which provides the signal sequences required for initiation of translation, to a portion of the PTM comprising the sequences encoding the adenovirus protein will result in the formation of a functional chimeric RNA capable of encoding the adenovirus proteins having complementing activity.

Additional features can be added to the PTM molecule either after, or before, the nucleotide sequence encoding the adenovirus protein. Such features include polyadenylation signals, 5' splice sequences capable of enhancing splicing, additional binding regions or additional splice sites. Stop codons or other elements in the region between the binding domain and the splice site may be added to prevent unspliced pre-mRNA expression. In another embodiment of the invention, PTMs can be generated with a second antisense binding domain downstream from the nucleotide sequences encoding a translatable protein to promote binding to the 3' target intron or exon and to block the fixed authentic cis-5' splice site (U5 and/or U1 binding sites). Further elements such as a 3' hairpin structure, circularized RNA, sequences that promote or facilitate nuclear localization and spliceosomal incorporation, and stability may be incorporated.

Sequences referred to as exonic splicing enhancers may also be included in the structure of the synthetic PTMs. Transacting splicing factors, namely the serine/arginine-rich (SR) proteins, have been shown to interact with such exonic splicing enhancers and modulate splicing (See, Tacke et al, 1999, Curr. Opin. Cell Biol. 11:358–362; Tian et al., 2001, J. Biological Chemistry 276:33833–33839; Fu, 1995, RNA 1:663–680). Nuclear localization signals may also be included in the PTM molecule (Dingwell and Laskey, 1986, Ann. Rev. Cell Biol. 2:367–390; Dingwell and Laskey, 1991, Trends in Biochem. Sci. 16:478–481). Such nuclear localization signals can be used to enhance the transport of synthetic PTMs into the nucleus where trans-splicing occurs. In addition, sequences may be used that enhance the retention of PTMs in the nucleus (Boelans et al., 1995 RNA 1:273–83; Good et al., 1997 Gene Ther. 4:45–54).

The PTMs may also be engineered to express therapeutic or diagnostic polypeptides in a selected cell type. Such diagnostic polypeptides include, for exapmle, bioluminescent or fluorescent molecules, enzymes, and protein/peptide tags. Therapeutic polypeptides include, for example, growth factors, known ligand molecules, signal transduction regulators or enzymes, to name a few. Such PTMs can be used to target selective expression of the diagnostic or therapeutic polypeptide to a selected target cell. The PTMs may also be engineered to express the therapeutic or diagnostic polypeptides as adenoviral fusion proteins. Alternatively, the PTM may be designed to encode both an adenovirus protein and a therapeutic or diagnostic protein. Such a PTM would include an internal ribosomal entry segment (IRES) (Ghattas et al., Mol. Cell Biol. 11:5848–5859) which would support translation initiation at a second site in the chimeric RNA.

5.2. Production of Recombinant Adenovirus

The present invention provides recombinant conditionally replicative adenoviruses that may be utilized to target selective cell death. The recombinant adenoviruses of the invention are engineered to encode PTM molecules capable of mediating a trans-splicing reaction with a specific target pre-mRNA. Such recombinant adenoviruses may be generated using a variety of different cloning methods known to those of skill in the art including those described in Adenoviral Vectors for Gene Therapy, Curiel and Douglas, eds. 2002, Academic Press and Ausubel et al. (eds.), 1993, Current Protocols in Molecular Biology, John Wiley & Sons, NY; and Kriegler, 1990, Gene Transfer and Expression, A Laboratory Manual, Stockton Press, NY. In preferred embodiments of the invention, the adenoviruses are type 2, 5, 9 or 35 adenoviruses.

The present invention relates to a recombinant conditionally replicative adenovirus which is defective for replication but capable of expressing a PTM molecule. Within the meaning of the present invention, the expression "conditionally replicative adenovirus" refers to a defective adenovirus which is incapable of autonomous replication in a host cell until the viral defect is complemented in trans. The present invention is based on the ability of the adenoviruses of the invention to provide complementing activity upon successful trans-splicing between the virally expressed PTM and the target pre-mRNA.

The present invention provides recombinant adenovirus wherein at least one adenovirus gene is deleted. In a preferred embodiment of the invention the adenovirus early region E1, E2 or E4 gene is deleted and replaced with nucleic acid sequences encoding the PTM(s) of interest. Recombinant adenoviruses of the invention also include those viruses having multiple deletions and insertion of one or more PTM encoding sequence. Since such an adenovirus is conditionally replicative, the virus is initially propagated in cells that complement the deleted region(s) of the adenovirus, i.e., "complementing cell line". Within the meaning of the present invention "complementing cell line" refers to a cell line that provides the gene products necessary for replication of the defective adenovirus. Such cells include those infected with a helper virus.

In a specific embodiment of the invention, the early region 1 (E1) is deleted and replaced with a nucleic acid sequences encoding a PTM of interest and the virus is propagated in an E1-trans-complementing cell line such as 293 (Graham et al., 1977, J. Gen. Virol. 36:59–72) or in cell lines expressing the pre-mRNA target. In another embodiment, the conditionally replicating adenovirus may be propagated in vitro in cell lines naturally expressing or engineered to express the specific target pre-RNA(s).

Standard methods for making such deleted adenovirus vectors, such as E1 deleted vectors, may involve in vitro ligation methods or homologous recombination methods. (See, Adenoviral Vectors for Gene Therpy, Curiel and Douglas, eds. 2002, Academic Press). The following section describes methods for generating E1 deleted adenoviruses wherein the E1 region is replaced with a nucleic acid molecule encoding a PTM of interest, however, such methods can also be used to generate adenoviruses with deletions and insertion of PTM encoding nucleic acids in other regions of the virus. The complementing cell lines to be used when producing such viruses will depend on the type of deletion, for example, E1, E2 or E4, and can be determined by one of ordinary skill in the art.

The in vitro ligation method utilizes (i) a fragment of the adenoviral genome derived by enzymatic digestion of the DNA at a unique restriction site downstream from the viral E1 region, i.e, the right end of the genome, and (ii) a DNA fragment containing the left end of the adenoviral genome including the right inverted terminal repeat (ITR), the packaging signal, E1A enhancer sequence (map unit; 0 to 1.3) and a nucleic acid molecule encoding the PTM of interest. The two fragments are ligated together resulting in a recombinant adenovirus having a nucleic acid molecule encoding a PTM inserted into the E1 region. In a preferred embodiment of the invention the unique ClaI site (map unit; 2.6) in the viral genome is used to replace a portion of the viral E1 region with the nucleic acid molecule encoding the PTM of interest. Once ligated, the DNA is then directly transfected into an E1 trans-complementing cell line, such as 293 cells, to produce a recombinant adenovirus capable of expressing the PTM of interest. Alternatively, the DNA may be transfected into a cell expressing a target pre-mRNA which will lead to expression of the PTM encoded complementing adenovirus polypeptide.

Homologous recombination methods utilize two fragments of DNA with overlapping sequences that are designed to recombine in vivo. In an embodiment of the invention, the fragments of DNA may comprise recombinant vector sequences, e.g., plasmid fragments. The first fragment may contain the entire Ad genome with a deletion of the DNA packaging and E1 region. The second fragment may contain a right ITR, packaging signals and overlapping sequences with the first plasmid. The second fragment is also engineered to contain nucleic acid sequences encoding the PTM of interest. For homologous recombination methods, the two fragments are co-transfected into a cell that is capable of complementing the E1 region, e.g., 293 cells.

For both in vitro or homologous recombination, transfection methods that may be utilized for the delivery of a nucleic acid molecule into the complementing cell include methods such as electroporation, lipofection, or calcium phosphate mediated transfection. The recombinant adenovirus may then be isolated through plaque purification.

In addition, methods for adenoviral preparation based on homologous recombination of two plasmids using yeast artificial chromosomes or bacteria may also be utilized to generate the recombinant adenoviruses of the invention. U.S. patents disclosing preparation of recombinant adenoviruses include: U.S. Pat. Nos. 5,962,313; 5,962,311; 5,952,221; 5,932,210; 5,928,944; 5,922,576; 5,919,676; 5,891,690; 5,885,808; 5,880,102; 5,877,011; 5,871,982; 5,869,037; 5,858,351; 5,851,806; 5,843,742; 5,837,484; 5,820,868; 5,789,390; 5,756,283; 5,747,072; 5,731,172; 5,700,470; 5,670,488; 5,616,326; 5,589,377; 5,585,362; and 5,354,678. Other references of interest include Berkner, et al. (1983, Nucleic Acids Res. 11, 6003–6020); Bett, et al. 1994, Proc. Natl. Acad. Sci. USA, 91, 8802–6); Chartier, et al. (1996, J Virol. 70, 4805–4810); Crouz et al. (1997, Proc. Natl. Acad. Sci. USA, 94, 1414–1419); Gilardi et al. (1990, FEBS Lett. 267, 60–2); He, et al. (1998, Proc. Natl. Acad. Sci. USA, 95, 2509–2514); Ketner, et al. (1994, Proc. Natl. Acad. Sci. USA, 91, 6186–6190; Miyake, et al. (1996, Proc. Natl. Acad. Sci. USA, 93, 1320–1324); and Rosenfeld, et al. (1991, Science. 252, 431–4) the disclosures of which are incorporated by reference in their entirety.

In yet another embodiment of the invention, the conditionally replicative adenoviruses of the invention may be further engineered to alter the mechanism of the virus/cell interaction thereby targeting selective adenovirus infection to a specific cell type of interest, i.e., a cancer cell or infected cell. For example, the structure of the adenovirus receptor binding components, such as the viral capsid, may be genetically engineered to promote specific interactions between engineered capsids and target cell surface molecules expressed in the target cell. For example, a receptor binding ligand can be linked to a capsid protein through genetic engineering of the capsid gene. Alternatively, biospecific chemical conjugates may be linked to the adenovirus particles. (See, Adenoviral Vectors for Gene Therpy, Curiel and Douglas, eds. 2002, Academic Press).

5.3. Uses and Administration of Trans-Splicing Molecules

The compositions and methods of the present invention will have a variety of different applications including targeting of adenovirus mediated cell lysis to cancer cells or cells infected with an infectious agent. In addition, the present invention provides methods and compositions for targeting expression of therapeutic or diagnostic polypeptides to a cell expressing a selective pre-mRNA. In a specific embodiment, the recombinant adenovirus of the invention is directly administered in vivo, where it infects the targeted cells and is expressed to produce the PTM of interest. This can be accomplished by direct infection of the targeted cells with the adenovirus.

Infection of the target cell with the recombinant adenovirus will result in expression of the PTM molecule. In the presence of the targeted pre-mRNA molecule, a trans-splicing reaction will occur between the PTM and the targeted pre-mRNA molecule resulting in the formation of a chimeric mRNA molecule. The chimeric mRNA molecule is engineered to express an adenovirus protein required for complementation of defective adenovirus. Therefore, in the presence of an accurate trans-splicing reaction the defective adenovirus will replicate leading to cell lysis and infection of surrounding cells by the newly replicated virus. Thus, the present invention provides methods and compositions for targeting adenovirus mediated cell lysis only to cells expressing the targeted pre-mRNA molecule.

The present invention also provides for pharmaceutical compositions comprising an effective amount of the recombinant adenovirus encoding a PTM, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Examples of suitable pharmaceutical carriers are described in "Remington's Pharmaceutical sciences" by E. W. Martin.

In specific embodiments, pharmaceutical compositions are administered: (1) in diseases or disorders involving the expression of a cancer selective target pre-mRNA, e.g., tumor cells; (2) in diseases or disorders where cells are infected with an infectious agent and express a target pre-mRNA encoded by the infectious agent or (3) diseases or disorders arising from the activity of a specific cell type.

In a specific embodiment, it may be desirable to administer the pharmaceutical compositions of the invention locally to the area in need of treatment, e.g., the site of the tumor. This may be achieved by, for example, and not by way of limitation, inhalation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Other control release drug delivery systems, such as nanoparticles, matrices such as controlled-release polymers, hydrogels.

The recombinant adenoviruses of the invention will be administered in amounts which are effective to produce the desired effect in the targeted cell, e.g., adenovirus mediated cell lysis. Effective dosages of the adenoviruses can be determined through procedures well known to those in the art which address such parameters as biological half-life, bioavailability and toxicity.

The amount of the composition of the invention which will be effective will depend on the nature of the disease or disorder being treated, and can be determined by standard clinical techniques. In addition, in vitro assays may optionally be employed to help identify optimal dosage ranges.

The present invention is not to be limited in scope by the specific embodiments described herein. Indeed, various modifications of the invention in addition to those described herein will become apparent to those skilled in the art from the foregoing description and accompanying Figures. Such modifications are intended to fall within the scope of the appended claims. Various references are cited herein, the disclosure of which are incorporated by reference in their entireties.

I claim:

1. A recombinant conditionally replicative adenovirus comprising a replication defective adenovirus having a deletion in its genome of an early gene which prevents replication of the adenovirus, said defective adenovirus comprising a transgene wherein said transgene encodes a pre-trans-splicing molecule (PTM) comprising:
   a) one or more target binding domains that target binding of the pre-trans-splicing molecule (PTM) to a target pre-mRNA expressed within a cancer cell;
   b) a 3' splice region comprising a branch point a pyrimidine tract, and a 3' splice acceptor site;
   c) a spacer region that separates the 3' splice region from the target binding domain; and
   d) a nucleotide sequence to be trans-spliced to the target pre-mRNA wherein said nucleotide sequence encodes an adenovirus polypeptide required for adenovirus replication, which upon transplicing of the PTM to the target pr-mRNA results in a replicative adenovirus.

2. A recombinant replicative adenovirus comprising a replication defective adenovirus having a deletion in its genome of an early gene which prevents replication of the adenovirus, said defective adenovirus comprising a transgene wherein said transgene encodes a pre-trans-splicing molecule (PTM) comprising:
  a) one or more target binding domains that target binding of the pre-trans-splicing molecule (PTM) to a target pre-mRNA expressed within a cancer cell;
  b) a 5' splice site;
  c) a spacer region that separates the 5' splice site from the target binding domain: and
  d) a nucleotide sequence to be trans-spliced to the target pre-mRNA wherein said nucleotide sequence encodes an adenovirus polypeptide required for adenovirus replication, which upon transplicing of the PTM to the target pre-mRNA result in a replicative ye adenovirus.

3. The adenovirus of claim 1 wherein the pre-trans-splicing molecule further comprises a 5' donor site.

4. The adenovirus of claim 1 wherein the pre-trans-splicing molecule further comprises a safety nucleotide sequence comprising one or more complementary sequences that bind to one or more sides of the 3' splice region.

5. The adenovirus of claim 2 wherein said pre-trans-splicing molecule further comprises a safety sequence comprising one or more complementary sequences that bind to one or both sides of the 5' splice site.

6. The adenovirus of claim 1 or 2 wherein the adenovirus polypeptide is selected from the group consisting of an adenovirus E1, E2 and E4 early region polypeptide.

7. The adenovirus of claim 1 wherein the adenovirus polypeptide is an E1 polypeptide.

8. The adenovirus of claim 1 or 2 wherein said target pre-mRNA is expressed in the cancer cell but is undetectable in a normal cell.

9. A recombinant conditionally replicative adenovirus comprising a replication defective adenovirus having a deletion in its genome of an early gene which prevents replication of the adenovirus, said defective adenovirus comprising a transgene wherein said transgene encodes a pre-trans-splicing molecule (PTM) comprising:
  a) one or more target binding domains that target binding of the pre-trans-splicing molecule (PTM) to a target pre-mRNA expressed within a cell wherein sand target pre-mRNA is (i) expressed by a pathogenic microorganisim in the cell or (ii) induced in the cell(s) of a subject infected with the pathogenic microorganism;
  b) a 3' splice region comprising a branch point a pyrimidine tract and a 3' splice acceptor site;
  c) a spacer region that separates the 3' splice region from the target binding domain; and
  d) a nucleotide sequence to he trans-spliced to the target pre-mRNA wherein said nucleotide sequence encodes an adenovirus polypeptide required for adenoviral replication, which upon transplicing of the PTM to the target pre-mRNA results in a replicative adenovirus.

10. A recombinant conditionally replicative adenovirus comprising a replication defective adenovirus having a deletion in its genome of an early gene which prevents replication of the adenovirus, said defective adenovirus comprising a transgene wherein said transgene encodes a pre-trans-splicing molecule (PTM) comprising:
  a) one or more target binding domains that target binding of the pre-trans-splicing molecule (PTM) to a target pre-mRNA wherein said target pre-mRNA is (i) expressed by a pathogenic microorganism in the cell or (ii) induced in the cell(s) of a subject infected with the pathogenic microorganism;
  b) a 5' splice site;
  c) a spacer region that separates the 5' splice site from the target binding domain; and
  d) a nucleotide sequence to he tans-spliced to the target pre-mRNA wherein said nucleotide sequence encodes an adenovirus polypeptide required for adenoviral replication, which upon transplicing of the PTM to the target pre-mRNA results in a replicative adenovirus.

11. The adenovirus of claim 9 wherein the pre-trans-splicing molecule further comprises a 5' donor site.

12. The adenovirus of claim 9 wherein the pre-trans-splicing molecule further comprises a safety nucleotide sequence comprising one or more complementary sequences that bind to one or more skies of the 3' splice region.

13. The adenovirus of claim 10 wherein said pre-trans-splicing molecule further comprises a safety sequence comprising one or more complementary sequences that bind to one or both sides of the 5' splice site.

14. The adenovirus of claim 9 or 10 wherein, the pathogenic microorganism is a virus, fungus, bacterium or parasite.

* * * * *